(12) United States Patent
Cole et al.

(10) Patent No.: US 7,572,639 B2
(45) Date of Patent: Aug. 11, 2009

(54) METHOD AND APPARATUS FOR PREDICTING PREGNANCY OUTCOME

(75) Inventors: Laurence A. Cole, Albuquerque, NM (US); Jaime M. Riley, Columbia, MO (US); Francis W. Byrn, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 665 days.

(21) Appl. No.: 11/144,091

(22) Filed: Jun. 2, 2005

(65) Prior Publication Data

US 2006/0063275 A1  Mar. 23, 2006

Related U.S. Application Data

(60) Provisional application No. 60/576,528, filed on Jun. 3, 2004.

(51) Int. Cl.
*G01N 33/48* (2006.01)
(52) U.S. Cl. .............................. 436/65; 702/19; 702/23; 436/510
(58) Field of Classification Search ................... 436/65, 436/510, 906; 700/89; 702/23; 435/806
See application file for complete search history.

(56) References Cited

U.S. PATENT DOCUMENTS

| 4,720,455 | A | | 1/1988 | Babu et al. | |
|---|---|---|---|---|---|
| 5,283,176 | A | | 2/1994 | Sato et al. | |
| 5,693,479 | A | * | 12/1997 | Feinberg et al. | 435/7.21 |
| 5,786,220 | A | * | 7/1998 | Pronovost et al. | 436/518 |
| 6,376,199 | B1 | * | 4/2002 | Caniggia et al. | 435/7.2 |
| 6,429,018 | B1 | | 8/2002 | Cole et al. | 436/87 |
| 6,492,178 | B1 | * | 12/2002 | Pandian | 436/65 |
| 6,500,627 | B1 | * | 12/2002 | O'Connor et al. | 435/7.92 |
| 6,627,457 | B2 | | 9/2003 | Pandian et al. | |
| 2003/0003597 | A1 | * | 1/2003 | O'Connor et al. | 436/510 |
| 2003/0022381 | A1 | * | 1/2003 | Pandian et al. | 436/65 |
| 2003/0153093 | A1 | * | 8/2003 | Chang et al. | 436/510 |
| 2004/0082020 | A1 | * | 4/2004 | Cole | 435/7.23 |
| 2004/0098207 | A1 | * | 5/2004 | Friggens et al. | 702/32 |
| 2004/0181167 | A1 | * | 9/2004 | Carney et al. | 600/551 |
| 2006/0015411 | A1 | | 1/2006 | Mela | |

OTHER PUBLICATIONS

Johansson, Plasma levels of progesterone in pregnancy measured by a rapid competitive protein binding technique, Acta Endocrinologica 1996;61, 607-17.*

(Continued)

*Primary Examiner*—Jill Warden
*Assistant Examiner*—Shogo Sasaki
(74) *Attorney, Agent, or Firm*—Henry D. Coleman; R. Neil Sudol; William J. Sapone (57) ABSTRACT

A method for predicting pregnancy outcome includes measuring blood levels of hCG-hg and progesterone in a pregnant woman, determining a rate of change of progesterone levels from the blood measurements, determining at least a qualitative direction of change of hCG-hg levels from the blood measurements, comparing the determined rate of change of progesterone levels with a pre-established reference value, and determining at least a qualitative likelihood of a term pregnancy and a failed pregnancy for the woman from the qualitative direction of change of hCG-hg levels and the determined rate of change of progesterone levels relative to the pre-established reference value. The rate of change of progesterone is determined by formula as a number of days for progesterone to double.

11 Claims, 7 Drawing Sheets

OTHER PUBLICATIONS

Buyalos et al., Serum .beta.-Human Chorionic Gonadotropin, Estradiol and Progesterone as Early Predictors of Pathologic Pregnancy, (1992) Journal of Reproductive Medicine vol. 37, No. 3, pp. 261-266.*

O'Leary et al., Serum progesterone and human chorionic gonadotrophin measurements in the evaluation of ectopic pregnancy, Australian and New Zealand J of Obstetrics and Gynaecology Aug. 1996;3693) 319-323.*

Birken et al, Immunochemical Measurement of Early Pregnancy Isoforms of hCG: Potential Applications to Fertility Research, Prenatal Diagnosis and Cance, Archives of Medical Research 32 (2001) 635-643.*

Stern et al., Early diagnosis of ectopic pregnancy using receiver—operator characteristic curves of serum progesterone concentrations, Human Reproduction vol.8 No. 5 pp. 775-779, 1993.*

U.S. Appl. No. 11/250,050, filed Oct. 13, 2005, Cole.

* cited by examiner

FIGURE 1A

| WOG | Patient Code | Date | ITA | hCG | Prog |
|---|---|---|---|---|---|
| Normal term outcome | | | | | |
| 4.5 | KJMI | 10/28/2003 | 13.561 | 30.09 | |
| 4.5 | NADI | 7/31/2003 | 0.681 | 0.89 | 14.9 |
| 4.5 | LAJE | 9/22/2003 | 28.661 | 36 | 13.7 |
| 4.5 | COMA | 11/10/2003 | 10.316 | 21.73 | |
| 5.5 | HEEM | 8/4/2003 | 40.099 | 97.45 | 8.8 |
| 3.5 | COSH | 6/18/2003 | 4.48 | 9.45 | 27.4 |
| 4 | SIME | 12/18/2003 | 4.15 | 11.55 | |
| 4 | KEKA | 8/15/2003 | 6.733 | 15.91 | 16.3 |
| 4.5 | ESCY | 7/21/2003 | 34.741 | 105.27 | 33 |
| 5 | WASW | 10/20/2003 | 54.39 | 230.64 | |
| 6.5 | ANCH | 8/26/2003 | 54.483 | 114.09 | 15.1 |
| 4.5 | ALVA | 9/22/2003 | 8.244 | 17 | 14.4 |
| 5.5 | YOER | 2/18/2004 | 6.137 | 20.45 | 22.2 |
| 4.5 | KLCA | 9/22/2003 | 17.617 | 28.55 | 32.9 |
| 3.5 | GOME | 1/6/2004 | 5.571 | 13.82 | 88 |
| 3 | BRHE | 1/30/2004 | 18.18 | 52 | 257 |
| 3.5 | SAME | 11/3/2003 | 14.328 | 36.64 | |
| 4 | GEMI | 8/1/2003 | 6.822 | 14.09 | 105 |
| 4.5 | FLAN | 10/13/2003 | 55.439 | 343.64 | |
| 5 | HEJA | 9/2/2003 | 94.383 | 315.09 | 25.5 |
| 6 | KHSU | 2/12/2004 | 238.137 | 1907.45 | 19.8 |

FIGURE 1B

| WOG | Patient Code | ITA/hCG | Date | # day | ITA | hCG | Prog |
|---|---|---|---|---|---|---|---|
| Normal term outcome | | | | | | | |
| 4.5 | KJMI | 45% | 10/29/2003 | 1.00 | 32.46 | 81.82 | |
| 4.5 | NADI | 77% | 8/4/2003 | 4.00 | 10.514 | 21.73 | 27.5 |
| 4.5 | LAJE | 80% | 9/24/2003 | 2.00 | 40.466 | 104.73 | 9.7 |
| 4.5 | COMA | 47% | 11/12/2003 | 2.00 | 24.645 | 60.82 | |
| 5.5 | HEEM | 41% | 8/6/2003 | 2.00 | 85.51 | 268.64 | 8.8 |
| 3.5 | COSH | 47% | 6/20/2003 | 2.00 | 13.208 | 26 | 22 |
| 4 | SIME | 36% | 12/22/2003 | 4.00 | 19.788 | 70.45 | |
| 4 | KEKA | 42% | 8/18/2003 | 3.00 | 25.838 | 61.73 | 12.5 |
| 4.5 | ESCY | 33% | 7/23/2003 | 2.00 | 71.877 | 256.18 | 36.1 |
| 5 | WASW | 24% | 10/22/2003 | 2.00 | 121.97 | 545.91 | |
| 6.5 | ANCH | 48% | 8/28/2003 | 2.00 | 102.837 | 252.45 | 12 |
| 4.5 | ALVA | 48% | 9/24/2003 | 2.00 | 17.599 | 37.55 | 12.1 |
| 5.5 | YOER | 30% | 2/23/2004 | 5.00 | 27.292 | 134 | 18 |
| 4.5 | KLCA | 62% | 9/24/2003 | 2.00 | 24.555 | 57 | 23.7 |
| 3.5 | GOME | 40% | 1/8/2004 | 2.00 | 10.525 | 27.45 | 28.9 |
| 3 | BRHE | 35% | 2/2/2004 | 3.00 | 37.303 | 133.82 | 196 |
| 3.5 | SAME | 39% | 11/5/2003 | 2.00 | 21.586 | 67.82 | |
| 4 | GEMI | 48% | 8/4/2003 | 3.00 | 17.663 | 34.55 | 33 |
| 4.5 | FLAN | 16% | 10/15/2003 | 2.00 | 102.864 | 592.73 | |
| 5 | HEJA | 30% | 9/4/2003 | 2.00 | 184.493 | 520.91 | 18.2 |
| 6 | KHSU | 12% | 2/19/2004 | 7.00 | 668.27 | 9400 | 22.8 |

FIGURE 1C

| Patient Code | ITA/hCG | Doubling time ITA | | Doubling time hCG | | Doubling time Prog |
|---|---|---|---|---|---|---|
| Normal term outcome | | | | | | |
| KJMI | 40% | 0.79 | | 0.69 | | 4.67 |
| NADI | 48% | 1.01 | | 0.87 | | 4.52 |
| LAJE | 39% | 4.02 | | 1.30 | | -8.03 |
| COMA | 41% | 1.59 | | 1.35 | | -2.45 |
| HEEM | 32% | 1.83 | | 1.37 | | 0.00 |
| COSH | 51% | 1.28 | | 1.37 | | -12.63 |
| SIME | 28% | 1.78 | | 1.53 | | -8.34 |
| KEKA | 42% | 1.55 | | 1.53 | | -10.45 |
| ESCY | 28% | 1.91 | | 1.56 | | 30.88 |
| WASW | 22% | 1.72 | | 1.61 | | -10.54 |
| ANCH | 41% | 2.18 | | 1.75 | | -12.07 |
| ALVA | 47% | 1.83 | | 1.75 | | -15.93 |
| YOER | 20% | 2.32 | | 1.84 | | -13.22 |
| KLCA | 43% | 4.17 | | 2.01 | | -8.45 |
| GOME | 38% | 2.18 | | 2.02 | | -2.49 |
| BRHE | 28% | 2.89 | | 2.20 | | -10.23 |
| SAME | 32% | 3.38 | | 2.25 | | -4.56 |
| GEMI | 51% | 2.19 | | 2.32 | | -12.40 |
| FLAN | 17% | 2.24 | | 2.54 | | -8.79 |
| HEJA | 35% | 2.07 | | 2.76 | | -12.40 |
| KHSU | 7% | 4.70 | | 3.04 | | 19.65 |
| | >2.3 or - | 6 of 21 29% | >2.1 or - | 6 of 21 29% | <-12 or >40 | 6 of 21 29% |
| | >4 or - | 3 of 21 14% | >2.5 or - | 3 of 21 14% | | |

FIGURE 2A

| WOG | Patient Code | Date | ITA | hCG | Prog |
|---|---|---|---|---|---|
| Spontaneous abortion in 1st trimester | | | | | |
| 6 | ANCA | 1/8/2004 | 10.745 | 58.18 | 11.4 |
| 3.5 | HURO | 1/12/2004 | 1.024 | 1.89 | 19.8 |
| 5 | QUMA | 7/7/2003 | 5.546 | 12.07 | 24.3 |
| 5.5 | MOJA | 9/30/2003 | 220.462 | 2094.55 | |
| 3 | DOKR | 10/23/2003 | 1.047 | 1.57 | |
| 5 | FABA | 8/4/2003 | 3.392 | 10.09 | 3 |
| 5 | SLAN | 6/23/2003 | 29.675 | 76.55 | 135 |
| 4.5 | KEPA | 7/14/2003 | 33.801 | 95.73 | 14.6 |
| 6.5 | GAWA | 8/20/2003 | 1.736 | 4.85 | 8.1 |
| 4.5 | WHLI | 8/13/2003 | 9.837 | 21.45 | 18.2 |
| 4 | MIMI | 11/25/2003 | 2.457 | 6 | |
| 4 | JOKA | 8/26/2003 | 63.203 | 86.73 | |
| Ectopic pregnancies | | | | | |
| 4 | MADE | 11/19/2003 | 1.521 | 2.67 | |
| 5.5 | SCLE | 9/25/2003 | 3.572 | 8.27 | 18.3 |

FIGURE 2B

| WOG | Patient Code | ITA/hCG | Date | # day | ITA | hCG | Prog |
|---|---|---|---|---|---|---|---|
| Spontaneous abortion in 1st trimester | | | | | | | |
| 6 | ANCA | 18% | 1/12/2004 | 4.00 | 8.387 | 56.09 | 9.6 |
| 3.5 | HURO | 54% | 1/14/2004 | 2.00 | 0.741 | 1.22 | 5.5 |
| 5 | QUMA | 46% | 7/9/2003 | 2.00 | 2.457 | 6.13 | 6.7 |
| 5.5 | MOJA | 11% | 10/1/2003 | 1.00 | 258.436 | 1470.91 | |
| 3 | DOKR | 67% | 10/29/2003 | 6.00 | 0.22 | 0.11 | |
| 5 | FABA | 34% | 8/6/2003 | 2.00 | 0.858 | 2.69 | 1.8 |
| 5 | SLAN | 39% | 6/25/2003 | 2.00 | 62.643 | 189.82 | 111 |
| 4.5 | KEPA | 35% | 7/16/2003 | 2.00 | 60.706 | 208.73 | 11.7 |
| 6.5 | GAWA | 36% | 8/22/2003 | 2.00 | 2.079 | 9.82 | 6.6 |
| 4.5 | WHLI | 46% | 8/15/2003 | 2.00 | 16.759 | 39.55 | 18.3 |
| 4 | MIMI | 41% | 12/1/2003 | 6.00 | 6.904 | 25.36 | |
| 4 | JOKA | 73% | 8/28/2003 | 2.00 | 46.35 | 107.27 | |
| Ectopic pregnancies | | | | | | | |
| 4 | MADE | 57% | 11/21/2003 | 2.00 | 4.576 | 12.18 | |
| 5.5 | SCLE | 43% | 9/29/2003 | 4.00 | 12.088 | 34.55 | 15.7 |

FIGURE 2C

| Patient Code | ITA/hCG | Doubling time ITA | | Doubling time hCG | | Doubling time Prog |
|---|---|---|---|---|---|---|
| Spontaneous abortion in 1st trimester | | | | | | |
| ANCA | 15% | -11.19 | | -75.79 | | -16.13 |
| HURO | 61% | -4.29 | | -3.17 | | -2.16 |
| QUMA | 40% | -1.70 | | -2.05 | | -2.15 |
| MOJA | 18% | 4.36 | | -1.96 | | 245.00 |
| DOKR | 200% | -2.67 | | -1.56 | | -4.50 |
| FABA | 32% | -1.01 | | -1.05 | | -5.43 |
| SLAN | 33% | 1.86 | | 1.53 | | -14.16 |
| KEPA | 29% | 2.37 | | 1.78 | | -12.52 |
| GAWA | 21% | 7.69 | | 1.97 | | -13.54 |
| WHLI | 42% | 2.60 | | 2.27 | | 506.00 |
| MIMI | 27% | 4.03 | | 2.89 | | -11.34 |
| JOKA | 43% | -4.47 | | 6.52 | | -14.23 |
| | >2.2 or - | 11 of 12 92% | >2.1 or - | 9 of 12 75% | <-12 or >40 | 7 of 12 58% |
| | >4 or - | 9 of 12 75% | >2.5 or - | 8 of 12 67% | | |
| Ectopic pregnancies | | | | | | |
| MADE | 38% | 1.26 | | 0.91 | | |
| SCLE | 35% | 2.27 | | 1.94 | | -18.09 |

FIG. 3

METHOD AND APPARATUS FOR PREDICTING PREGNANCY OUTCOME

RELATED APPLICATIONS

This application claims priority from U.S. provisional application 60/576,528, filed Jun. 3, 2004, the entire contents of which are incorporated by reference herein.

BACKGROUND OF THE INVENTION

The invention relates to a diagnostic tool for predicting pregnancy outcome. More specifically, this invention relates to a method and apparatus for predicting whether a pregnancy will proceed to term or will fail, i.e., result in a spontaneous abortion or an ectopic pregnancy.

A currently available test for determining the outcome of a pregnancy involves the measurement of hCG levels in the blood of a pregnant woman. The test has a reliability or accuracy of about 68%. It would be desirable to provide a pregnancy-outcome test that had a higher probability of predicting the correct result.

SUMMARY OF THE INVENTION

A method for predicting pregnancy outcome comprises, in accordance with the present invention, measuring blood, plasma or urine levels of hCG-hg and progesterone in a pregnant woman, determining a rate of change of progesterone levels from the blood, plasma or urine measurements, determining at least a qualitative direction of change of hCG-hg levels from the blood, plasma or urine measurements, comparing the determined rate of change of progesterone levels with a pre-established reference value, and determining at least a qualitative likelihood of a term pregnancy and a failed pregnancy for the woman from the qualitative direction of change of hCG-hg levels and the determined rate of change of progesterone levels relative to the pre-established reference value.

The measuring of hCG-hg and progesterone levels is carried out on at least two occasions in an interval of time including the third week and the sixth week of gestation. More particularly, the measuring of hCG-hg and progesterone levels is carried out within a seven-day period occurring in the interval of time including the third week and the sixth week of gestation.

Pursuant to another feature of the present invention, the rate of change of progesterone is determined as a number of days for progesterone to double. This rate of change of progesterone is determined from the formula:

Doubling rate=$(\Delta D \cdot \log 2)/(\log(D2/D1))$, where D1 and D2 are levels of progesterone measured on a first day and a different second day and where $\Delta D$ is the number of days between the first day and the second day.

Pursuant to particular features of the present invention, a term outcome is predicted if hCG-hg levels are not declining, a term outcome is predicted if the number of days for progesterone to double is fewer than 40 days, a failed pregnancy is predicted if hCG-hg levels are declining, and a failed pregnancy is predicted if the number of days for progesterone to double is more than 40 days.

An associated apparatus for predicting pregnancy outcome comprises an assay device for measuring blood levels of hCG-hg and progesterone in a blood, plasma or urine sample taken from a pregnant woman and further comprises a computing device operatively connected to the assay device for receiving therefrom encoded hCG-hg and progesterone levels. The computing device is programmed to determine, from the blood, plasma or urine measurements, a rate of change of progesterone levels and at least a qualitative direction of change of hCG-hg levels in order to assess pregnancy outcome. The computing device includes a memory storing reference values and is additionally programmed to compare the determined rate of change of progesterone levels with a pre-established reference value and to determine at least a qualitative likelihood of a term pregnancy and a failed pregnancy for the woman from the qualitative direction of change of hCG-hg levels and the determined rate of change of progesterone levels relative to the pre-established reference value.

The computing device is preferably programmed to determine the rate of change of progesterone as a number of days for progesterone to double. The computing device may be programmed to determine the number of days for progesterone to double from the formula:

Doubling rate=$(\Delta D \cdot \log 2)/(\log(D2/D1))$, where D1 and D2 are levels of progesterone measured on a first day and a different second day and where $\Delta D$ is the number of days between the first day and the second day.

In accordance with another feature of the present invention, the computing device is programmed to predict a term outcome if hCG-hg levels are not declining, to predict a term outcome if the number of days for progesterone to double is fewer than 40 days, to predict a failed pregnancy if hCG-hg levels are declining, and to predict a miscarriage if the number of days for progesterone to double is more than 40 days.

The present invention provides an algorithm for determining the time it takes for progesterone levels to double, as well as the time it takes for hCG-hg levels to double. The measurement of both hCG-hg levels and progesterone levels and the use of the algorithm results in a predictive capability that is at least twice the power of the current hCG test method.

DEFINITIONS

Unless defined otherwise, all technical and scientific terms used herein have the same meaning as commonly understood by those of ordinary skill in the art to which this invention belongs. For purposes of the present invention, the following terms are defined below.

As used herein, "hyperglycosylated hCG" (as used herein "hCG-hg"), also, but less commonly "invasive trophoblast antigen" or "ITA" is a glycoprotein hormone secreted by trophoblast cells of the placenta of pregnant women. hCG-hg is also called hyperglycosylated hCG. hCG-hg is similar, to C5 hCG, which is a nicked h-hCG obtained from a choriocarcinoma patient. hCG-hg, as defined, also includes fragments of hCG-hg, or variants of hCG-hg. In particular, hCG-hg encompasses molecules that exhibit similar biological activities or expression patterns to hCG-hg and that exhibit aberrant carbohydrate levels as compared to normally glycosylated hCG including, nicked hCG, α-subunits of hCG, β-subunits of hCG, or any combination thereof. Examples of hCG-hg isoforms include isoforms that comprise 57% triantennary N-linked oligosaccharides and 68% hexasaccharide-type O-linked oligosaccharides. Another hCG-hg isoform may comprise 48% triantennary N-linked oligosaccharides and 100% hexasaccharide-type O-linked oligosaccharides. In normal pregnancies, a relatively small proportion of more complex triantennary N-linked oligosaccharides (0-30%) and larger hexasaccharide-type O-linked sugar units (0-20%) are also found.

The term "biological marker" or "pregnancy marker" is used herein to denote a molecule that has an expression pattern or biological activity related to pregnancy. Such biological pregnancy markers include hCG-hg, hCG, progesterone, and fragments thereof. Other examples of pregnancy markers include, but are not limited to, beta-subunit hCG-hg, beta-core hCG-hg, beta-subunit hCG, beta-core hCG, unconjugated estriol (UE3), alpha-fetoprotein (AFP), leptin, prorenin, renin, DHEA-S, leukocyte acid phosphatase, inhibin, pregnancy associated plasma protein A (PAPP-A), AFP-L3, P43, superoxide dismutase (SOD), proMBP, fetal DNA, insulin-like growth factor binding proteins 3 (IGFBP3), CA 125, placental lactogen, Hp2FF, serum sialytransferase, s100b protein, schwangers chafts protein 1 (SPI), activin A/follistatin, fetal antigen (FA-2), and placental alkaline phosphatase (PALP).

DETAILED DESCRIPTION OF THE PREFERRED EMBODIMENTS

In order to predict pregnancy outcome, one measures blood levels of hCG-hg and progesterone in a pregnant woman and determines a rate of change of progesterone levels from the blood measurements. In addition, one determines at least a qualitative direction of change of hCG-hg levels from the blood measurements. The determined rate of change of progesterone levels is compared with a pre-established reference value. At least a qualitative likelihood of a term pregnancy and a failed pregnancy for the woman is determined from the qualitative direction of change of hCG-hg levels and the determined rate of change of progesterone levels relative to the pre-established reference value.

The measuring of hCG-hg and progesterone levels is carried out twice within a seven-day period occurring in the interval of time including the third week and the sixth week of gestation. The concentrations of hCG-hg and progesterone in a test sample may be measured using any known techniques. For example, the measurement of hCG-hg may be performed pursuant to the procedures described in U.S. Pat. No. 6,627,457, the disclosure of which is hereby incorporated by reference. The measurement of progesterone may be performed pursuant to the procedures described in U.S. Pat. No. 4,720,455 or 5,283,176, the disclosures of which are likewise incorporated by reference. Alternatively, concentration of progesterone in a sample may be measured by using commercially available assay kits such as Radioimmunoassay (produced by Diagnostic Products Corporation) and Radioimmunoassay (produced by Daiichi Radioisotope Labs, LTD.). The present technology for the measurement of hCG-hg and progesterone are well known, and typically uses antibodies, preferably monoclonal antibodies which selectively bind to hCG-hg or progesterone to determine concentration levels or amounts within a given blood or urine sample, although other methods for measuring hCG-hg and/or progesterone may be used.

The rate of change of progesterone is determined as a number of days for progesterone to double. This rate of change of progesterone is determined from the formula:

$$\text{Doubling rate} = (\Delta D \cdot \log 2)/(\log(D2/D1)),$$

where D1 and D2 are levels of progesterone measured on a first day and a different second day and where ΔD is the number of days between the first day and the second day.

This is a known equation used for measuring hCG doubling rate. A doubling-rate number of 2 means that the measured biological marker (hCG-hg or progesterone) doubles in 2 days, while a doubling-rate number of 7 means a much lower rise because the measured marker doubles in 7 days. Similarly, a minus number means that the levels are decreasing. As such, the higher the calculated doubling-rate number is above 2, the slower the biological marker is increasing. In worse or slower cases, the minus numbers indicate that marker levels are decreasing. Thus if progesterone does not double within 2 days, the doubling-rate number will be higher than 2 or a negative number, owing to the nature of logarithmic equations. The above equation allows one to determine the doubling rate for measurements taken 2, 3 4 or 5 days apart, and not just 2 days apart.

A term outcome is predicted if hCG-hg levels are not declining or if the number of days for progesterone to double is fewer than 40 days. A failed pregnancy is predicted if hCG-hg levels are declining or if the number of days for progesterone to double is more than 40 days.

An experiment to confirm the validity of the method described above for predicting the likelihood of a term pregnancy or a spontaneous abortion included the measuring of hCG, hCG-hg, and progesterone levels in the blood of 35 pregnant women. The measurements entailed at least two sets of measurements on different days after the beginning of the third week of gestation and prior to the end of the sixth week of gestation. In addition, for each test subject, the measurements were made within a seven-day window. Of the 35 women, 21 had normal term pregnancies, 12 had spontaneous abortions in the first trimester, and 2 had ectopic pregnancies.

The rates of change of the measured levels of blood constituents or biological markers hCG, hCG-hg, and progesterone were calculated in the form of the number of days for the respective biological marker to double, using the formula:

$$\text{Doubling rate} = (\Delta D \cdot \log 2)/(\log(D2/D1)),$$

where D1 and D2 are levels of the respective biological marker measured on different days and where ΔD is the number of days between the first day and the second day.

For each test subject, FIGS. 1A-1C and 2A-2C list the weeks of gestation (WOG) at the time of the measurements, a subject code or designation, the date of a first blood sampling, measured levels of hCG-hg, hCG and progesterone in the first blood sample, a ratio of hCG-hg to hCG in the first blood sample, the date of a second blood sampling, measured levels of hCG-hg, hCG and progesterone in the second blood sample, a ratio of hCG-hg to hCG in the second blood sample, and doubling time in days for each of the measured blood constituents.

An analysis of the raw data set forth in FIGS. 1A-1C and 2A-2C reveals the following results. With respect to the use of hCG as a biological marker for predicting pregnancy outcome, where hCG requires more than 2.1 days to double or where hCG levels are declining with time (negative doubling rate), a spontaneous abortion is predicted with a 75% accuracy. Concomitantly, where hCG doubles in fewer than 2.1 days, term pregnancy is predicted with an accuracy of 71%. With respect to the use of hCG-hg alone as a biological marker for predicting pregnancy outcome, where hCG-hg requires more than 2.3 days to double or where hCG-hg levels are declining with time, a spontaneous abortion is predicted with a 92% accuracy. Concomitantly, where hCG-hg doubles in fewer than 2.3 days, term pregnancy is predicted with an accuracy of 71%. With respect to the use of progesterone alone as a biological marker for predicting pregnancy outcome, where progesterone requires more than 40 days to double or where progesterone levels are declining with time, a spontaneous abortion is predicted with a 50% accuracy. Concomitantly, where progesterone doubles in fewer than 40 days, term pregnancy is predicted with an accuracy of 50%.

Pursuant to the current method, when the doubling rates of both hCG-hg and progesterone are taken into account, the accuracy of the predictions are increased relative to the use of hCG alone. Specifically, where hCG-hg has declining levels with time or where progesterone levels require more than 40 days to double, a spontaneous abortion is predicted with an 82% accuracy. Concomitantly, where hCG-hg are not declining or doubling at any rate or where progesterone is doubling in fewer than 40 days, term pregnancy is predicted with an accuracy of 90%.

The above calculations may be summarized as follows. With respect to sensitivity and false positive rate for detecting failing pregnancy:
 a. hCG (doubling rate greater than 2.1 days/declining levels with time)—75% detection of failures at 29% false detection of term pregnancies;
 b. hCG-hg (doubling rate greater than 2.3 days/declining levels with time)—92% detection of failures at 29% false detection of term pregnancies;
 c. progesterone (doubling rate greater than 40 days levels with time)—50% detection of failures at 29% false detection of term pregnancies;
 d. hCG-hg plus progesterone (hCG-hg declining levels with time OR progesterone doubling greater than 40 days with time) 82% detection of failures at 10% false detection of term pregnancies;
 e. hCG-hg plus hCG (too much overlap).

With respect to sensitivity and false positive rate for detecting a term outcome:
 a. hCG (doubling rate less than 2.1 days only)—71% detection of term outcome pregnancies at 25% false detection of failing pregnancies;
 b. hCG-hg (doubling rate less than 2.3 days only)—71% detection of term outcome pregnancies at 8% false detection of failing pregnancies;
 c. progesterone (doubling rate less than 40 days only)—71% detection of term outcome pregnancies at 50% false detection of failing pregnancies;
 d. hCG-hg plus progesterone (hCG-hg doubling at any rate and not declining OR progesterone doubling at less than 40 days)—90% detection of term outcome pregnancies at 18% false detection of failing pregnancies;
 e. hCG-hg plus hCG (too much overlap)

Taking into account that spontaneous abortions are the outcome of 16% of pregnancies in the United States and accordingly weighting the predictive accuracies set forth above, then hCG alone has a composite predictive value of 71%, comprising a predictive value positive (failure) 31%, at a predictive value negative rate (term) of 94%. hCG-hg alone has a combined predictive value of 74% comprising a predictive value positive (failure) of 38% and a predictive value negative rate (term) of 98%. Progesterone alone has a composite predictive value of 68% comprising a predictive value positive (failure) of 25% and a predictive value negative (term) of 88%. hCG-hg plus progesterone have a composite predictive value of 89% comprising a predictive value positive (failure) of 61% and a predictive value negative rate (term) of 96%. According to these computations, hCG alone will give the correct result (whether looking for failure or normal pregnancy outcome) 71% of the time, hCG-hg alone 74% of the time, and hCG-hg plus progesterone 89% of the time.

EXAMPLE 1

A woman at four-and-a-half weeks of gestation had blood taken. Levels of hCG-hg, hCG, and progesterone were 0.681, 0.89 and 14.9, respectively. Four days later, another blood sample was taken. Levels of hCG-hg, hCG, and progesterone were 10.514, 21.73, and 27.5, respectively. The doubling time in days was calculated as 1.01 for hCG-hg, 0.87 for hCG, and 4.52 for progesterone. Thus, hCG-hg was doubling at a daily rate, while progesterone was doubling in four-and-a-half days. The present method predicts a term pregnancy from this data, and the pregnancy was successful.

EXAMPLE 2

A woman at four-and-a-half weeks of gestation had blood taken. Levels of hCG-hg, hCG, and progesterone were 28.661, 36 and 13.7, respectively. Two days later, another blood sample was taken. Levels of hCG-hg, hCG, and progesterone were 40.466, 204.73, and 9.7, respectively. The doubling time in days was calculated as 4.02 for hCG-hg, 1.30 for hCG, and 8.03 for progesterone. Thus, hCG-hg was doubling in four days, while progesterone levels were falling. The present method predicts a term pregnancy from this data, and the pregnancy was successful.

EXAMPLE 3

A woman at six weeks of gestation had blood taken. Levels of hCG-hg, hCG, and progesterone were 238.137, 1907.45, and 19.8, respectively. Seven days later, another blood sample was taken. Levels of hCG-hg, hCG, and progesterone were 668.27, 9400, and 22.8, respectively. The doubling time in days was calculated as 4.70 for hCG-hg, 3.04 for hCG, and 19.65 for progesterone. Thus, hCG-hg was doubling in about 5 days, while progesterone was doubling in about twenty days. The present method predicts a term pregnancy from this data, and the pregnancy was successful.

EXAMPLE 4

A woman at six weeks of gestation had blood taken. Levels of hCG-hg, hCG, and progesterone were 10.745, 58.18, and 11.4, respectively. Four days later, another blood sample was taken. Levels of hCG-hg, hCG, and progesterone were 8.387, 56.09, and 9.6, respectively. The doubling time in days was calculated as −11.19 for hCG-hg, −75.79 for hCG, and −16.13 for progesterone. Thus, levels of hCG-hg and progesterone were falling. The present method predicts a failed pregnancy from this data, and a spontaneous abortion did occur.

EXAMPLE 5

A woman at four-and-a-half weeks of gestation had blood taken. Levels of hCG-hg, hCG, and progesterone were 33.801, 95.73, 14.6, respectively. Two days later, another blood sample was taken. Levels of hCG-hg, hCG, and progesterone were 60.706, 208.73, and 11.7, respectively. The doubling time in days was calculated as 2.37 for hCG-hg, 1.78 for hCG, and −12.52 for progesterone. Thus, the level of hCG-hg was doubling in 2.37 days, while the levels of progesterone were falling. The present method is inconclusive on this data. The declining level of progesterone indicates a failed pregnancy, while the positive doubling date for hCG-hg indicates a successful outcome. The pregnancy terminated prematurely, in a spontaneous abortion.

EXAMPLE 6

A woman at -and-a-half weeks of gestation had blood taken. Levels of hCG-hg, hCG, and progesterone were 220.462, 2094, respectively. Two days later, another blood sample was taken. Levels of hCG-hg, hCG, and progesterone were 60.706, 208.73, and 11.7, respectively. The doubling time in days was calculated as 2.37 for hCG-hg, 1.78 for hCG, and −12.52 for progesterone. Thus, the level of hCG-hg was doubling in 2.37 days, while the levels of progesterone were falling. The present method is inconclusive on this data. The declining level of progesterone indicates a failed pregnancy, while the positive doubling date for hCG-hg indicates a successful outcome. The pregnancy terminated prematurely, in a spontaneous abortion.

Figure 1A:
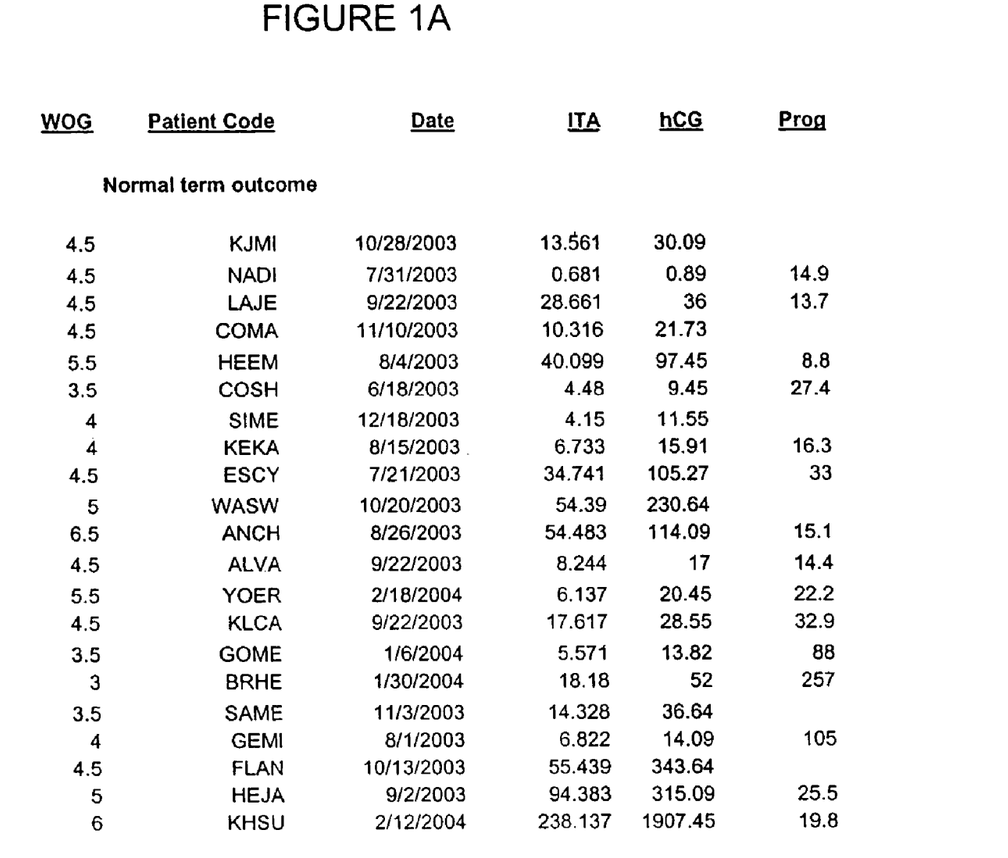
FIGS. 1A through 1C are a table of measurements and calculated quantities in an experimental investigation of pregnant women, listing values for successful or term pregnancies.
Figure 1B:
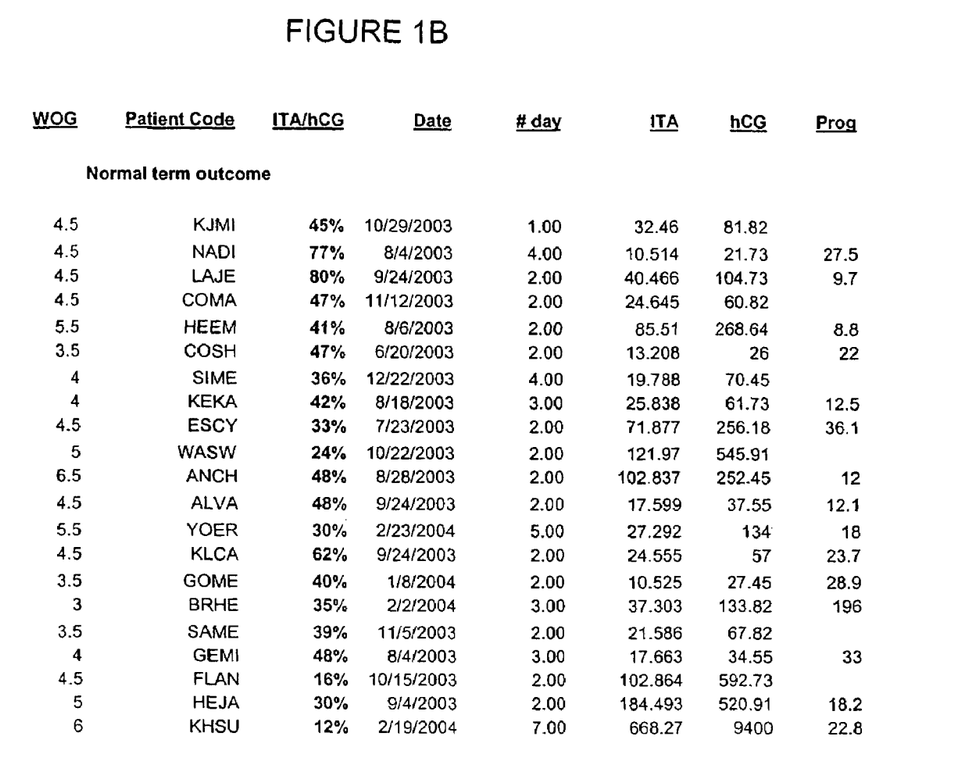
Figure 1C:
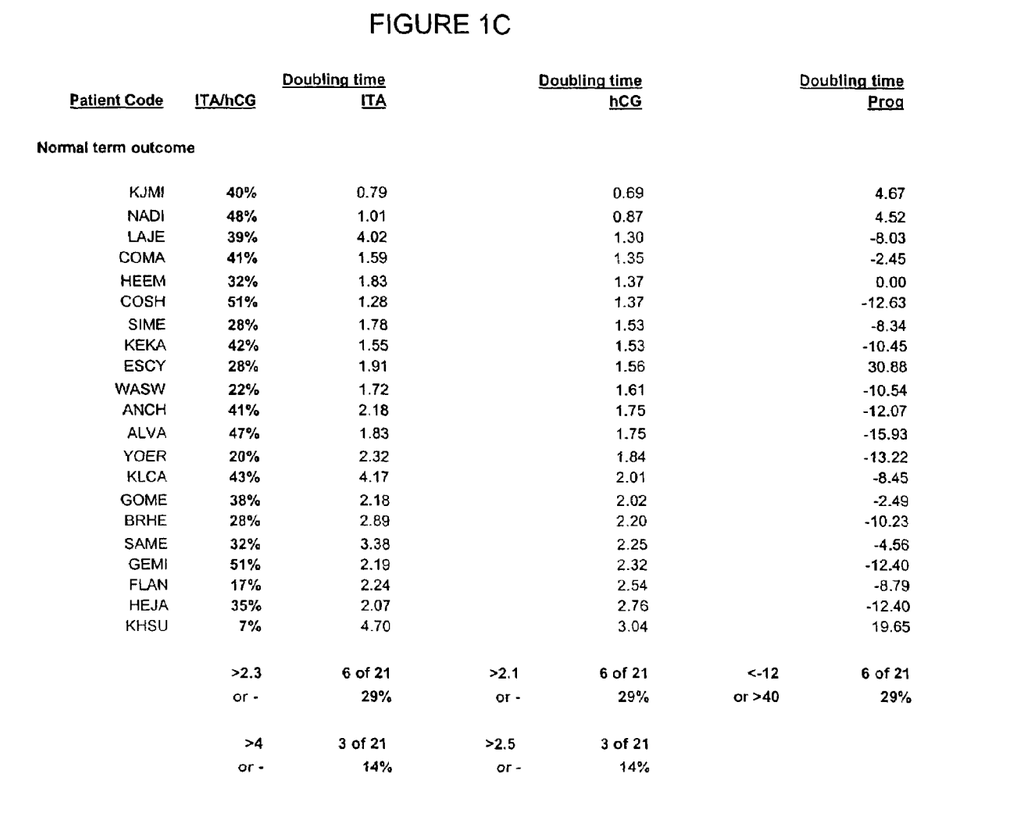
Figure 2A:
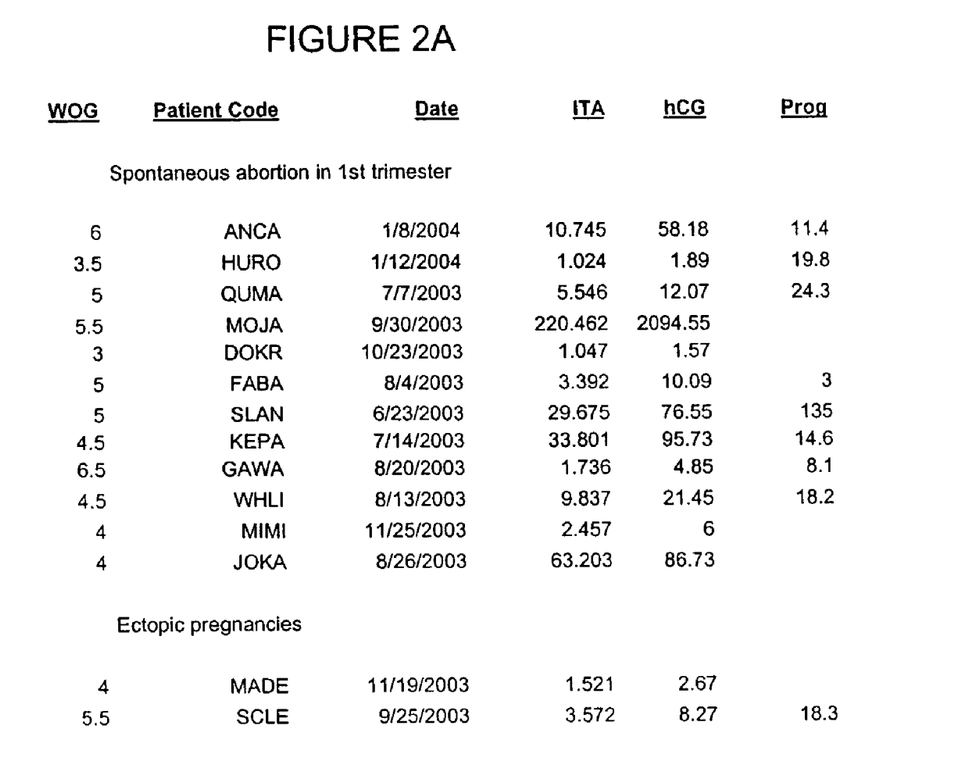
FIGS. 2A through 2C are a table of measurements and calculated quantities in the same experimental investigation of pregnant women, listing values for failed pregnancies, particularly pregnancies ending in spontaneous abortion or ectopic pregnancies.
Figure 2B:
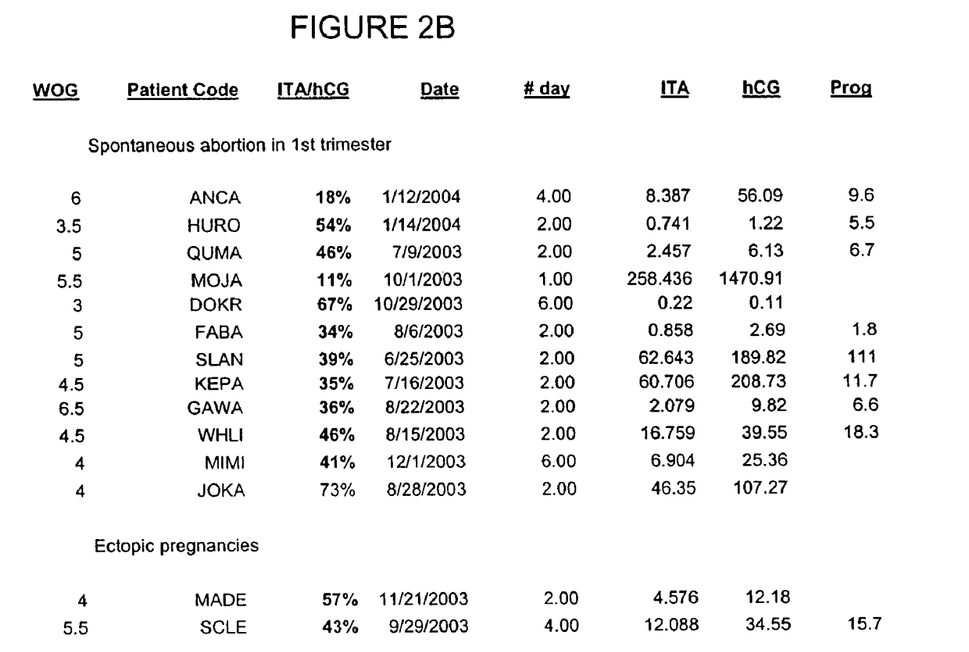
Figure 2C:
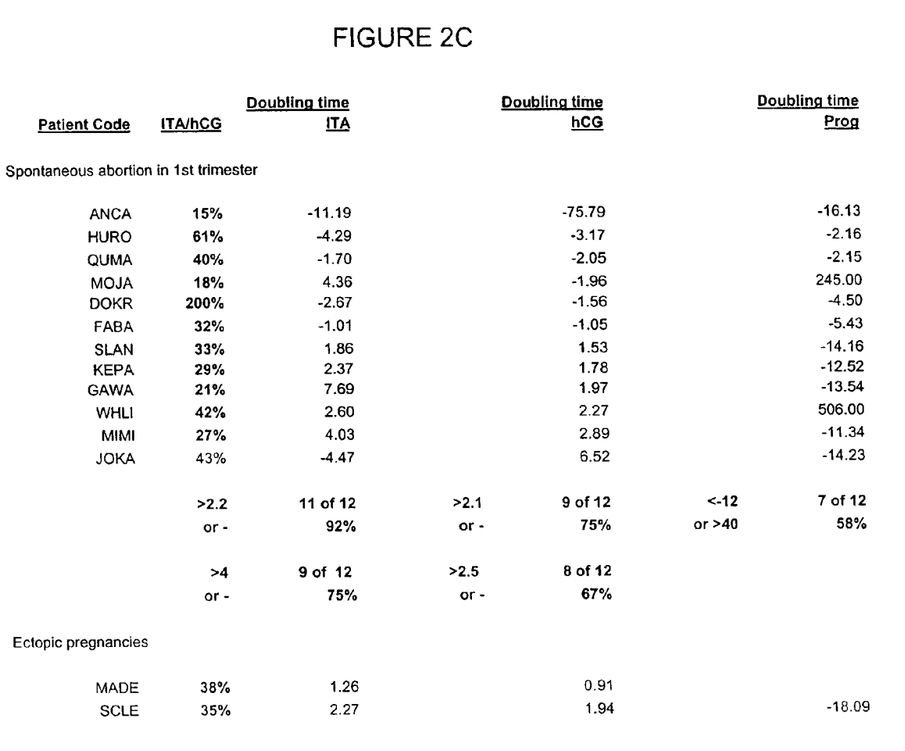
Figure 3:
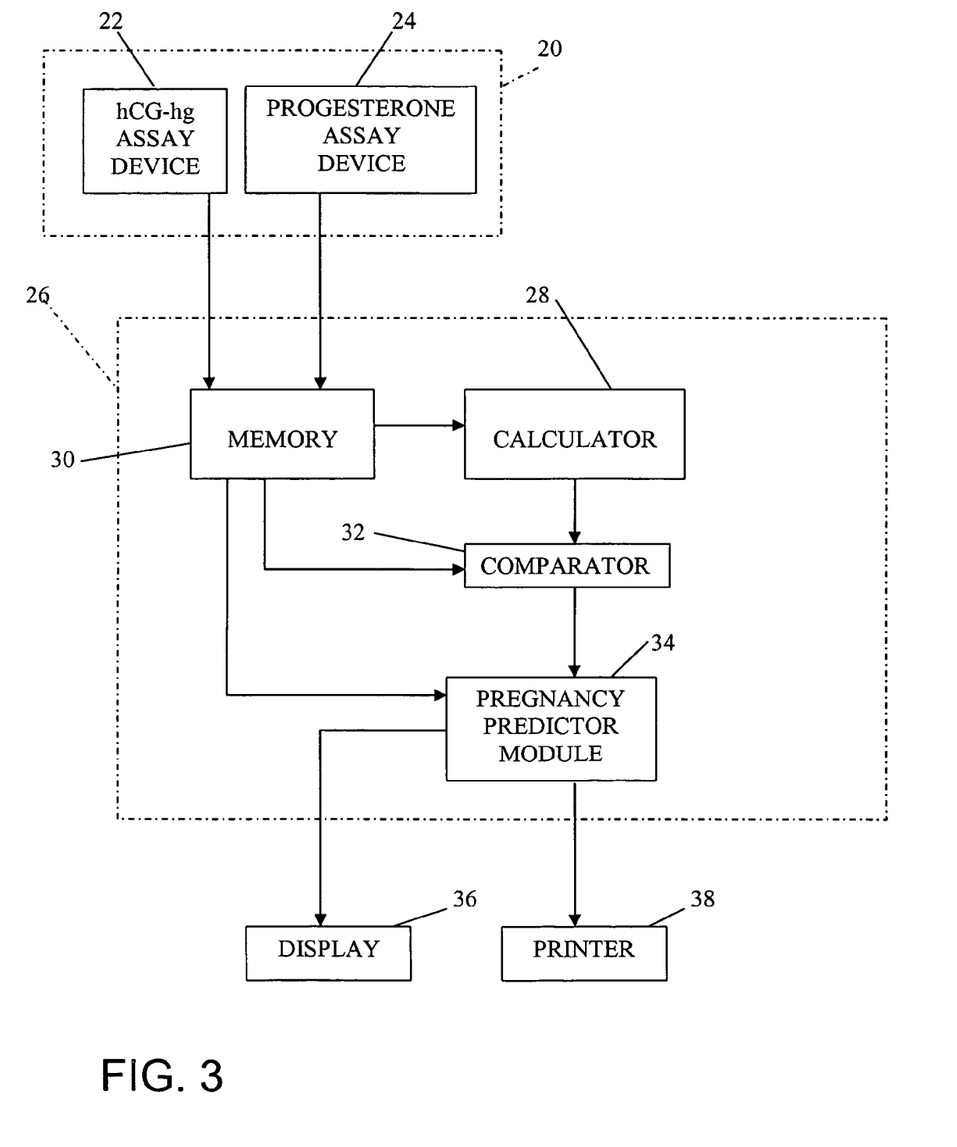
FIG. 3 is a block diagram of an apparatus in accordance with the present invention, for testing blood samples and automatically determining pregnancy outcome.

As illustrated in FIG. 3, an apparatus for predicting pregnancy outcome comprises an assay device 20 including a first component 22 for measuring blood levels of hCG-hg and a second component 24 for measuring progesterone in a blood sample taken from a pregnant woman. A computing device 26 is operatively connected to assay device 20 for receiving therefrom encoded hCG-hg and progesterone levels. Computing device 26 includes programmed hard-wired circuits or generic digital circuits modified by software to form a calculator 28 for determining, from the encoded hCG-hg and progesterone levels from assay device 20, a rate of change of progesterone levels and at least a qualitative direction of change of hCG-hg levels. Computing device 26 includes a memory 30 storing measured levels of the biological markers hCG-hg and progesterone, as well as reference values and further includes a comparator 32 (programmed by hard-wiring or software) for comparing the determined rate of change of progesterone levels with a pre-established reference value from memory 30. Computing device 26 includes evaluation or comparison circuitry 34 operatively connected to comparator 32 and memory 30 and optionally assay device 20 for determining at least a qualitative likelihood of a term pregnancy and a failed pregnancy from the qualitative direction of change of hCG-hg levels and the determined rate of change of progesterone levels relative to the pre-established reference value.

Calculator 28 determines the number of days for progesterone to double by using the formula:

$$\text{Doubling rate} = (\Delta D \cdot \log 2)/(\log(D2/D1)),$$

where D1 and D2 are levels of progesterone measured on a first day and a different second day and where $\Delta D$ is the number of days between the first day and the second day.

Computing device 26 is wired or programmed to predict a term outcome if hCG-hg levels are not declining or if the number of days for progesterone to double is fewer than 40 days and to predict a failed pregnancy if hCG-hg levels are declining or if the number of days for progesterone to double is more than 40 days. The predicted outcome may be communicated via a display 36 or a printer 38.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for predicting pregnancy outcome, comprising:

measuring blood, plasma or urine levels of hCG-hg and progesterone in a pregnant woman, wherein the measuring of hCG-hg and progesterone levels is carried out on at least two occasions in an interval of time;

determining a rate of change of progesterone levels from the measurements obtained;

determining at least a direction of change of hCG-hg levels from the blood, plasma or urine measurements;

comparing the determined rate of change of progesterone levels with a pre-established reference value; and determining at least a likelihood of a term pregnancy and a failed pregnancy for the woman from the direction of change of hCG-hg levels and the determined rate of change of progesterone levels relative to the pre-established reference value.

2. The method defined in claim 1 wherein the measuring of hCG-hg and progesterone levels is carried out on at least two occasions in the interval of time including the third week and the sixth week of gestation.

3. The method defined in claim 2 wherein the measuring of hCG-hg and progesterone levels is carried out within a seven-day period occurring in the interval of time including the third week and the sixth week of gestation.

4. The method defined in claim 3 wherein the rate of change of progesterone is determined as a number of days for progesterone to double, which is calculated from the formula:

Doubling rate=$(\Delta D \cdot \log 2)/(\log(D2/D1))$, where D1 and D2 are levels of progesterone measured on a first day and a different second day and where $\Delta D$ is the number of days between the first day and the second day.

5. The method defined in claim 4 wherein a term outcome is predicted if hCG-hg levels are not declining and if the number of days for progesterone to double is fewer than 40 days; and a failed pregnancy is predicted if hCG-hg levels are declining and if the number of days for progesterone to double is more than 40 days.

6. The method defined in claim 2 wherein the rate of change of progesterone is determined as a number of days for progesterone to double.

7. The method defined in claim 1 wherein the rate of change of progesterone is determined as a number of days for progesterone to double.

8. The method defined in claim 1 wherein the measuring of hCG-hg and progesterone levels is carried out within a seven-day period occurring in the interval of time.

9. The method defined in claim 1 wherein a term outcome is predicted if hCG-hg levels are not declining and if the number of days for progesterone to double is fewer than 40 days; and a failed pregnancy is predicted if hCG-hg levels are declining and if the number of days for progesterone to double is more than 40 days.

10. The method according to claim 1 wherein a term outcome is predicted if hCG-hg levels are not declining and if the number of days for progesterone to double is fewer than 40.

11. The method according to claim 1 wherein a failed pregnancy is predicted if hCG-hg levels are declining and if the number of days for progesterone to double is more than 40.

* * * * *

UNITED STATES PATENT AND TRADEMARK OFFICE
CERTIFICATE OF CORRECTION

PATENT NO. : 7,572,639 B2 Page 1 of 1
APPLICATION NO. : 11/144091
DATED : August 11, 2009
INVENTOR(S) : Laurence A. Cole and Jaime M. Riley

It is certified that error appears in the above-identified patent and that said Letters Patent is hereby corrected as shown below:

On the Title page, please delete Inventor "Francis W. Byrn, Albuquerque, NM (US)" as follows:

Item (75) Inventors: should read: "Laurence A. Cole, Albuquerque, NM (US);
Jaime M. Riley, Columbia, MO (US)"

Signed and Sealed this

Third Day of August, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,572,639 B2 |
| APPLICATION NO. | : 11/144091 |
| DATED | : August 11, 2009 |
| INVENTOR(S) | : Cole et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1037 days.

Signed and Sealed this

Seventh Day of September, 2010

David J. Kappos
*Director of the United States Patent and Trademark Office*